(12) United States Patent
Dale et al.

(10) Patent No.: US 9,198,689 B2
(45) Date of Patent: Dec. 1, 2015

(54) MEDICAL DEVICE

(71) Applicant: Cook Medical Technologies LLC, Bloomington, IN (US)

(72) Inventors: Melissa Dale, Linton, IN (US); Matthew J. Terwiske, Bloomington, IN (US)

(73) Assignee: Cook Medical Technologies LLC, Bloomington, IN (US)

( * ) Notice: Subject to any disclaimer, the term of this patent is extended or adjusted under 35 U.S.C. 154(b) by 296 days.

(21) Appl. No.: 13/921,972

(22) Filed: Jun. 19, 2013

(65) Prior Publication Data

US 2013/0345727 A1    Dec. 26, 2013

Related U.S. Application Data

(60) Provisional application No. 61/662,064, filed on Jun. 20, 2012.

(51) Int. Cl.

| | |
|---|---|
| *A61B 17/42* | (2006.01) |
| *A61B 17/04* | (2006.01) |
| A61B 17/28 | (2006.01) |
| A61B 17/00 | (2006.01) |
| A61B 17/08 | (2006.01) |

(52) U.S. Cl.
CPC ............... *A61B 17/42* (2013.01); *A61B 17/04* (2013.01); *A61B 17/28* (2013.01); *A61B 2017/00876* (2013.01); *A61B 2017/081* (2013.01)

(58) Field of Classification Search
CPC ...... A61B 17/32; A61B 17/104; A61B 17/42; A61B 2017/081; A61B 2017/00663
See application file for complete search history.

(56) References Cited

U.S. PATENT DOCUMENTS

| | | | |
|---|---|---|---|
| 1,428,495 A | 9/1922 | Radcliffe | |
| 3,933,158 A | 1/1976 | Haverstock | |
| 4,114,624 A | 9/1978 | Haverstock | |
| 4,222,383 A * | 9/1980 | Schossow | 606/216 |
| 4,531,521 A | 7/1985 | Haverstock | |
| 4,732,146 A * | 3/1988 | Fasline et al. | 602/79 |
| 4,976,726 A | 12/1990 | Haverstock | |
| 5,823,938 A | 10/1998 | Hernandez | |
| 6,329,564 B1 | 12/2001 | Lebner | |
| 6,730,014 B2 | 5/2004 | Wilk | |
| 6,790,229 B1 | 9/2004 | Berreklouw | |

(Continued)

FOREIGN PATENT DOCUMENTS

SU    445412    10/1974

*Primary Examiner* — Victor Nguyen
(74) *Attorney, Agent, or Firm* — Brinks Gilson & Lione

(57) ABSTRACT

An apparatus for approximating planes of a body tissue during a medical procedure may include an internal portion and an external portion. The internal portion may be implantable within a body of a patient and may include a first flexible sheet member, a first magnetic member, and a first working window through the first flexible sheet member. The external portion may include a second flexible sheet member, a second magnetic member, and a second working window through the second flexible sheet member. The first magnetic member and the second magnetic member may be attracted to one another to magnetically couple the internal and external portions and capture the body tissue between the internal and external portions. The first working window may be substantially aligned with the second working window to enable access to the internal and external surfaces of the body tissue through the respective first and second working windows.

19 Claims, 2 Drawing Sheets

(56) References Cited

U.S. PATENT DOCUMENTS

| | | |
|---|---|---|
| 7,087,073 B2 | 8/2006 | Bonutti |
| 7,186,251 B2 | 3/2007 | Malecki et al. |
| 7,626,070 B2 | 12/2009 | Propp |
| 7,811,296 B2 | 10/2010 | Goldfarb et al. |
| 8,007,503 B2 | 8/2011 | Catanese, III et al. |
| 8,038,634 B2 | 10/2011 | Rolnick et al. |
| 8,128,682 B2 | 3/2012 | Case et al. |
| 2006/0241691 A1 | 10/2006 | Wilk |
| 2007/0293878 A1 | 12/2007 | Butsch |
| 2008/0114396 A1 | 5/2008 | Cory et al. |
| 2008/0228220 A1 | 9/2008 | Weiser |
| 2010/0228287 A1 | 9/2010 | Jeekel et al. |
| 2011/0184440 A1 | 7/2011 | Saldinger |
| 2011/0264118 A1 | 10/2011 | Mazzucco et al. |

\* cited by examiner

1
MEDICAL DEVICE

CROSS-REFERENCE TO RELATED APPLICATIONS

This application claims priority and the benefit of provisional U.S. Patent Application Ser. No. 61/662,064, filed Jun. 20, 2012, which is incorporated herein by reference in its entirety.

TECHNICAL FIELD

This disclosure relates generally to medical devices. More specifically, this disclosure relates to medical devices for approximating planes of a body tissue for closure of an incision.

BACKGROUND

A variety of medical procedures include making an incision through a body tissue. To close the incision, the physician generally aligns the tissue planes on opposite sides of the incision and holds the tissue planes together with forceps. While holding the tissue planes together, the physician may suture the planes to one another to close the incision.

One medical procedure which includes making an incision is a cesarean section, or C-section. Such a procedure is an increasingly common alternative to natural childbirth (i.e., vaginal delivery). During a cesarean section, an incision is made through a patient's abdomen and uterus to deliver a child. After delivery of the child, the physician must close the incision through the uterine tissue. As is common when closing incisions through other body tissues, the physician generally will use forceps to hold the planes of uterine tissue on either side of the incision together while using a needle driver to pass a needle through the tissue to suture the incision closed.

Proper approximation of the uterine tissue (i.e., alignment of the tissue planes) following a cesarean section is important to promote proper healing of the uterine defect. If proper healing is not achieved, complications may occur in later pregnancies or later in life. Such complications may include abnormal placental plastentation, pelvic pain, or other complications.

SUMMARY

The present embodiments provide a medical device for approximating planes of a body tissue for closure of an incision.

In one example, an apparatus for approximating planes of a body tissue during a medical procedure may include an internal portion and an external portion. The internal portion may be implantable within a body of a patient. The internal portion may include a first flexible sheet member having a first engaging surface to engage an internal surface of the body tissue. The internal portion may include a first magnetic member. The internal portion may include a first working window through the first flexible sheet member. The external portion may include a second flexible sheet member having a second engaging surface to engage an external surface of the body tissue opposite the internal surface of the body tissue. The external portion may include a second magnetic member. The external portion may include a second working window through the second flexible sheet member. The first magnetic member and the second magnetic member may be attracted to one another to magnetically couple the internal portion and the external portion to one another and capture the body tissue between the internal portion and the external portion. With the internal portion and the external portion magnetically coupled to one another, the first working window may be substantially aligned with the second working window to enable access to the internal surface of the body tissue through the first working window and access to the external surface of the body tissue through the second working window.

In another example, an apparatus for approximating planes of a body tissue during a medical procedure may include an internal portion and an external portion. The internal portion may include a first flexible sheet member having a first engaging surface to engage an internal surface of the body tissue. The internal portion may include a first working window disposed in the first flexible sheet member. The external portion may include a second flexible sheet member having a second engaging surface to engage an external surface of the body tissue opposite the internal surface. The external portion may include a second working window disposed in the second flexible sheet member. In use, the internal portion and the external portion may be magnetically coupled to one another to sandwich a portion of the body tissue between the first engaging surface of the internal portion and the second engaging surface of the external portion. At least a portion of the first working window may be substantially aligned with a corresponding portion of the second working window.

In yet another example, a method for approximating planes of uterine tissue positioned on opposite sides of an incision in a uterine wall may include positioning an internal portion of a medical device inside a uterus. The internal portion may include a flexible sheet member having an engaging surface engaged with an inner surface of the uterine wall. The method may include positioning an external portion of the medical device outside the uterus. The external portion may include a flexible sheet member having an engaging surface engaged with an outer surface of the uterine wall. The method may include magnetically coupling the internal portion and the external portion to one another to capture a portion of the uterine wall between the engaging surface of the internal portion and the engaging surface of the external portion to approximate the planes of uterine tissue.

Other systems, methods, features, and advantages of the invention will be, or will become, apparent to one with skill in the art upon examination of the following figures and detailed description. It is intended that all such additional systems, methods, features, and advantages be within the scope of the invention, and be encompassed by the following claims.

BRIEF DESCRIPTIONS OF THE DRAWINGS

DETAILED DESCRIPTION OF THE DRAWINGS AND THE PRESENTLY PREFERRED EMBODIMENTS

Detailed embodiments of the present invention are disclosed herein. It is to be understood, however, that the disclosed embodiments are merely exemplary of the invention, which may be embodied in various and alternative forms. The figures are not necessarily to scale, and some figures may be configured to show the details of a particular component. Therefore, specific structural and functional details disclosed herein are not to be interpreted as limiting, but merely as a representative basis for the claims and for teaching one skilled in the art to practice the present invention.

In the present disclosure, the term "proximal" refers to a direction that is generally toward a physician during a medical procedure, while the term "distal" refers to a direction that is generally toward a target site within a patient's anatomy during a medical procedure.

Figure 1:
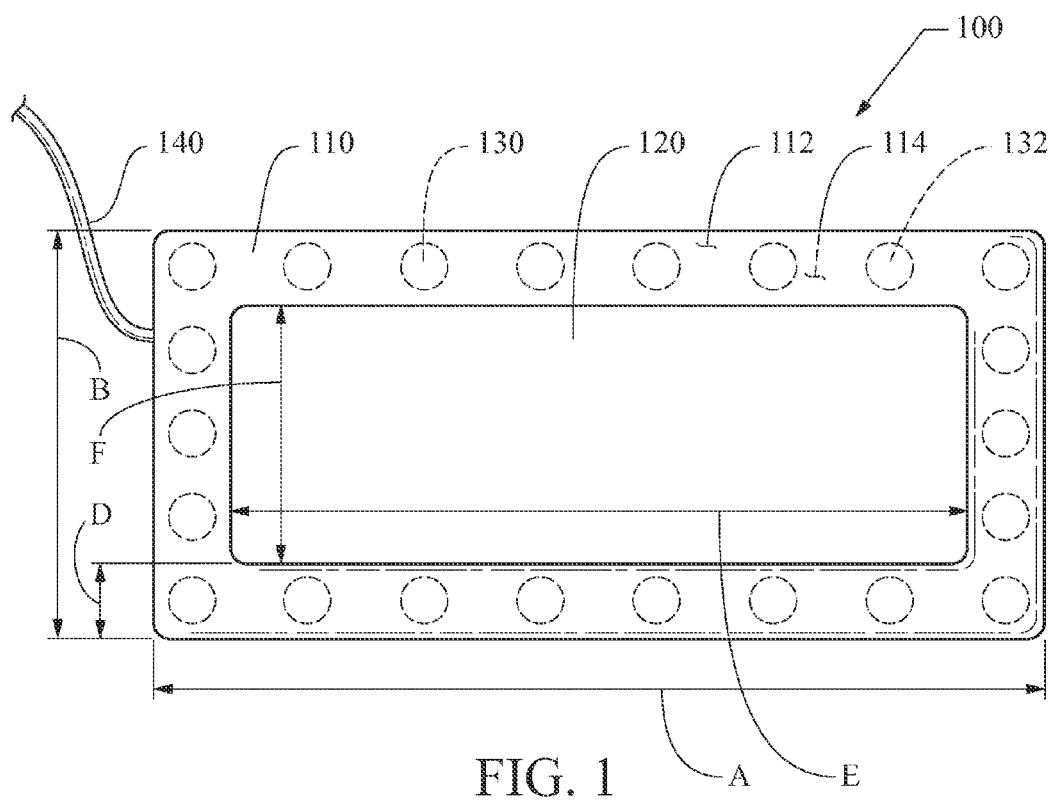
FIG. 1 illustrates an internal portion of one example of a medical device.
Figure 2:
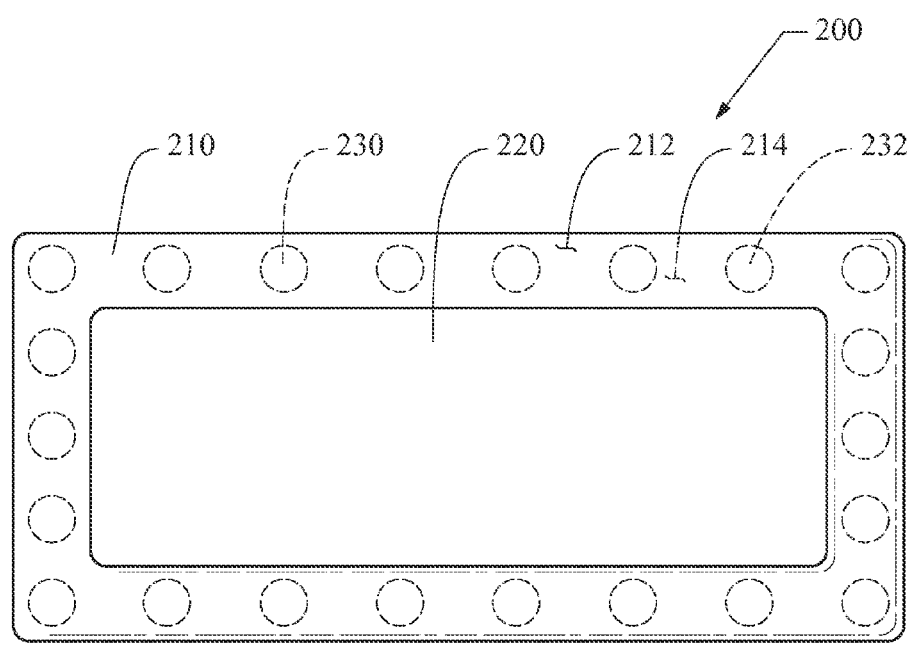
FIG. 2 illustrates an external portion of one example of a medical device.

FIGS. 1-2 illustrate one example of a medical device which may be used to aid in approximating planes of body tissue to close an incision through the body tissue. The medical device may include an internal portion 100 and an external portion 200. The internal portion 100, or a portion thereof, may be configured for implantation within a body of a patient, and the external portion 200 may be configured for placement on a surface of a body tissue opposite the internal portion to sandwich the body tissue between the internal portion and the external portion as further described below.

FIG. 1 illustrates one example of the internal portion 100 of the medical device. The internal portion 100 may include a sheet member 110. The sheet member 110 may be a relatively thin sheet of material and may include a first surface 112 and a second surface 114 positioned opposite the first surface. The first surface 112 may be configured to engage a surface of the body tissue as further described below. The sheet member 110 may have sufficient flexibility to enable the sheet member 110 to be rolled, folded, bent, warped, or otherwise deformed. In one example, the sheet member 110 may be movable (e.g., by rolling, folding, bending, or warping) between an open configuration and a collapsed configuration. In the open configuration, the sheet member 110 may be configured as a substantially planar sheet as shown in FIG. 1. In other words, the sheet member 110 may be substantially flat. In the collapsed configuration, the sheet member 110 may be deformed such that the sheet member 110 is non-planar. For example, the sheet member 110 may be deformed such that one or more edges of the sheet member 110 are drawn inward toward the central portion of the sheet member 110. In other words, the sheet member may be gathered to reduce the width and/or length occupied by the sheet member 110. This may aid in removing the internal portion 100 from the patient's body as further described below. In one example, the sheet member 110 may be sufficiently flexible to conform to the engaged surface of the body tissue as further described below. Additionally, or alternatively, the sheet member 110 may be biased toward the open configuration. In other words, the sheet member 110 may move toward the open configuration in the absence of external forces thereon. In another example, the sheet member 110 may be biased toward the collapsed configuration or any other configuration between the open configuration and the collapsed configuration.

Figure 3:
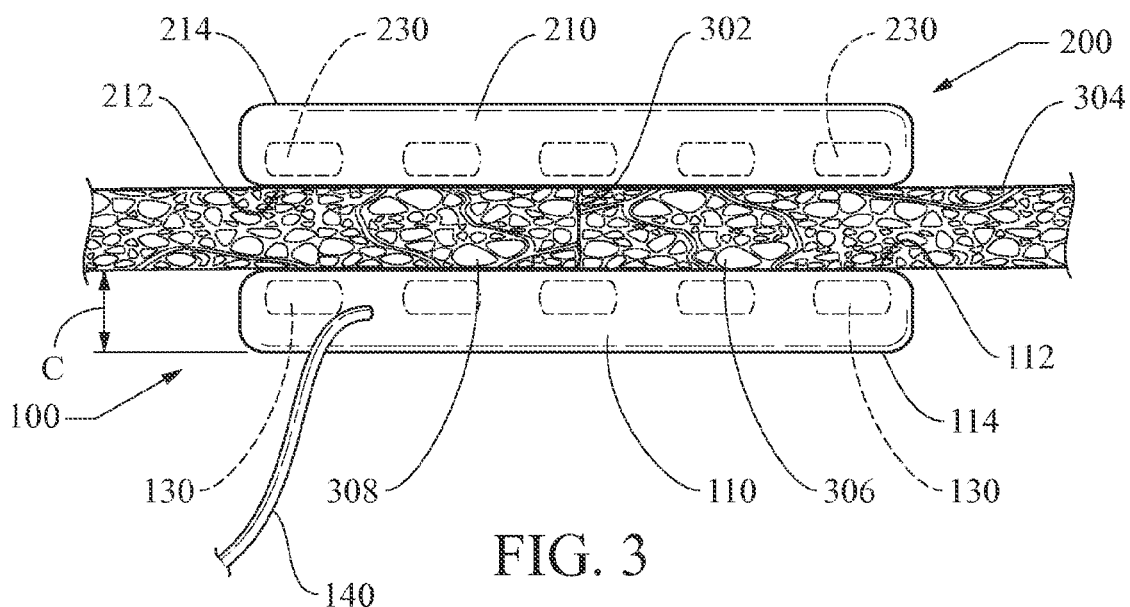
FIGS. 3-4 illustrate one example of a medical device in use to approximate planes of a body tissue to aid in closure of an incision.

The sheet member 110 may have any size and/or shape. For example, the sheet member 110 may be substantially rectangular as shown in FIG. 1. In other words, the sheet member 110 may include four edges, with adjacent edges positioned at approximately right angles relative to one another. In other examples, the sheet member 110 may have a circular, elliptical, triangular, or any other polygonal or non-polygonal shape. The corners of the sheet member 110 may be rounded as shown in FIG. 1. In other words, one or more of the corners of the sheet member 110 may be curved along a radius of curvature. This may reduce the probability of damaging the body tissue in contact with the sheet member 110. The sheet member 110 may have a length A and a width B as shown in FIG. 1. In one example, the length A may be between about 8 cm and about 43.5 cm, preferably between about 16 cm and about 29 cm. Additionally, or alternatively, the width B may be between about 1 cm and about 12 cm, preferably between about 2 cm and about 8 cm. In other examples, the sheet member 110 may have any other suitable length and/or width. The sheet member 110 may have a thickness C as shown in FIG. 3. In one example, the thickness C may be between about 2 mm and about 10 mm, preferably between about 3 mm and about 9 mm. In other examples, the sheet member 110 may have any other suitable thickness. The thickness of the sheet member 110 may be sufficient to encapsulate one or more coupling members (e.g., magnetic members) as further described below.

A working window 120 may be disposed in the sheet member 110. The working window 120 may be configured as an opening or an aperture through the sheet member 110. In one example, the working window 120 may pass through the thickness of the sheet member 110 from the first surface 112 to the second surface 114. The working window 120 may enable access to the body tissue sandwiched between the inner portion 100 and the outer portion 200 to enable the physician to close the incision in the body tissue as further described below. The working window 120 may have any suitable shape. The shape of the working window 120 may be the same as or different than the shape of the sheet member 110. For example, the working window 120 may have a substantially rectangular shape as shown in FIG. 1 and described above with reference to the sheet member 110. In other examples, the working window 120 may have a circular, elliptical, triangular, or any other polygonal or non-polygonal shape.

The sheet member 110 may be configured as a frame extending along a perimeter of the working window 120. In other words, the sheet member 110 may be configured as a frame which may define at least a portion of the perimeter of the working window 120. An inner perimeter of the sheet member 110 may be positioned adjacent to the working window 120, and an outer perimeter of the sheet member may be positioned along the outer edge of the sheet member. The frame may be disposed between and/or defined by the inner perimeter and the outer perimeter. Additionally, or alternatively, the frame may define the outer edge of the sheet member 110. In other words, the frame may extend around the perimeter of the sheet member 110 to define the outer edge of the sheet member 110. In one example, the sheet member 110 may extend around the entire perimeter of the working window 120 such that the working window 120 is enclosed within the frame as shown in FIG. 1. Alternatively, the sheet member 110 may extend partially around the perimeter of the working window 120 such that a gap is formed in the frame defined by the sheet member. In other words, a portion of the working window 120 may extend to the outer perimeter of the sheet member such that the sheet member does not extend around the entire perimeter of the working window. The working window 120 may enable a physician to access the engaged surface of the body tissue as further described below.

The frame surrounding the working window 120 may have a width D. In other words, the inner perimeter and the outer perimeter of the sheet member 110 may be separated from one another by the width D. In one example, the width D may be between about 0.25 cm and about 3 cm, preferably between about 0.5 cm and about 2 cm. In other examples, the frame may have any other suitable width. The width D of the frame may be substantially constant around the perimeter of the sheet member 110 as shown in FIG. 1. Alternatively, the width D of the frame may vary around the perimeter of the sheet member 110.

The working window 120 may have a length E and a width F. In one example, the length E may be between about 7.5 cm and about 37.5 cm, preferably between about 15 cm and about 25 cm. Additionally, or alternatively, the width F may be between about 0.5 cm and about 6 cm, preferably between about 1 cm and about 4 cm. In other examples, the working window 120 may have any other suitable length and/or width.

The internal portion 100 may include a coupling member 130. The coupling member 130 may be configured to couple the internal portion 100 to the external portion 200 of the medical device as further described below. In one example, the coupling member 130 may include one or more magnetic members, which may be configured to magnetically couple the internal portion 100 and the external portion 200 to one another. For example, the coupling member 130 may include a plurality of magnetic buttons 132 as shown in FIG. 1. The magnetic buttons 132 may be attached to the sheet member 110. The magnetic buttons 132 may be spaced from one another about the sheet member 110. In one example, the magnetic buttons 132 may be positioned around the perimeter of the sheet member 110. In other words, the magnetic buttons 132 may be positioned between the outer edge of the sheet member 110 and the working window 120 and spaced from one another with respect to the perimeter of the sheet member 110. In this manner, the attractive force between the internal portion 100 and the external portion 200 of the medical device may be substantially uniform around the perimeter of the respective internal and external portions.

Each magnetic button 132 may have any suitable size and/or shape. For example, each magnetic button 132 may have a substantially cylindrical shape as shown in FIG. 1. Each magnetic button 132 may have a diameter between about 6.35 mm and about 15.88 mm, preferably between about 6.5 mm and about 15.5 mm. Additionally, or alternatively, each magnetic button 132 may have a height between about 1.6 mm and about 3.18 mm, preferably between about 1.75 mm and about 3 mm. In one example, the thickness C of the sheet member 110 may be between about 1.5 and about 3 times the height of the magnetic buttons 132. This may enable the magnetic buttons 132 to be encapsulated within the sheet member 110 as further described below. In other examples, the magnetic buttons may have any other suitable shape such as, for example, a sphere, an ellipsoid, a prism (e.g., triangular, rectangular, pentagonal, or any other shaped prism), or any other geometric shape. In other examples, the magnetic buttons 132 may have any other suitable size. The size of the magnetic buttons 132 (or other coupling members 130) may depend on clinical need.

In other examples, the magnetic members may have any other suitable size and/or shape. For example, the coupling member 130 may include one or more magnetic strips. In one example, the coupling member 130 may include a plurality of magnetic strips, and one magnetic strip may extend along each edge of the sheet member 110. For example, the coupling member 130 may include four magnetic strips, and one magnetic strip may extend along each edge of a substantially rectangular sheet member 110. In other words, the magnetic strips may be positioned between the outer edge of the sheet member 110 and the working window 120 and may extend along the respective length and/or width of the sheet member 110. In another example, the magnetic members may be configured as one or more magnetic threads which may be attached to the sheet member 110. For example, the magnetic threads may be woven into the sheet member 110 or encapsulated in the sheet member 110. In another example, the magnetic members may include magnetic particles. For example, the sheet member 110 may be impregnated with a plurality of magnetic particles to impart magnetic properties thereto. In another example, the sheet member 110 may be formed from a magnetic material. In other examples, the coupling member 130 may include any number of magnetic members positioned at any suitable location with respect to the sheet member 110.

The internal portion 100 of the medical device may include a tether 140, which may aid in retrieving the internal portion 100 from within the patient's body after closure of the incision as further described below. The tether 140 may be an elongate member which may extend outward away from the sheet member 110 as shown in FIG. 1. The tether 140 may extend from any location on the sheet member 110. For example, the tether 140 may extend from the outer edge of the sheet member 110 as shown in FIG. 1. In other examples, the tether 140 may extend from the first surface 112, the second surface 114, or any other portion of the sheet member 110. Additionally, or alternatively, the tether 140 may extend from any edge of the sheet member 110 (e.g., a long edge, a short edge, the inner perimeter, the outer perimeter, or any other edge).

The tether 140 may be sufficiently flexible to conform to a passageway within the patient's body. To that end, the tether 140 may be formed from a relatively soft polymeric material as described below with reference to the sheet member 100. The tether 140 may be formed separately from or integrally with the sheet member 110. For example, the tether 140 may be formed separately from the sheet member 110 and attached to the sheet member 110. The tether 140 may be attached to the sheet member 110 using adhesives, sutures, staples, clips, or any other suitable attachment mechanism. In one example, the tether 140 may be attached to the sheet member 110 by chemical bonding. Alternatively, the tether 140 may be formed integrally with the sheet member 110. In one example, the tether 140 may include a length of tubing. The tubing may be hollow (i.e., a lumen may extend longitudinally within the tubing), solid (i.e., may not include a lumen extending longitudinally within the tubing), or any combination thereof. In another example, the tether 140 may include a filamentary member such as, for example, a thread (e.g., a suture thread) or a rope (e.g., a plurality of braided, twisted, or otherwise intertwined threads). For example, the tether 140 may be formed from a suture material such as Coated VICRYL® or MERSILENE® Polyester Fiber Suture, both commercially available from Ethicon, Somerville, N.J. In other examples, the tether 140 may include any other type of elongate member. The tether may have any suitable diameter or length. In one example, the tether 140 may have a diameter between about 4 Fr and about 18 Fr, preferably between about 8 Fr and about 12 Fr. Additionally, or alternatively, the tether 140 may have a length between about 10 cm and about 80 cm, preferably between about 20 cm and about 40 cm.

FIG. 2 illustrates one example of the external portion 200 of the medical device. The external portion 200 may be similar to the internal portion 100 in many respects. For example, the external portion 200 may include a sheet member 210 having a first surface 212 and a second surface 214 positioned opposite the first surface. The first surface 212 may be configured to engage a surface of the body tissue as further described below. In one example, the sheet member 210 may be sufficiently flexible to conform to the engaged surface of the body tissue. The sheet member 210 may have any suitable size and/or shape. For example, the sheet member 210 may be sized and shaped as described above with reference to the sheet member 110.

A working window 220 may be disposed in the sheet member 210. The working window 220 may be configured as an opening or an aperture through the sheet member 210. The working window 220 may enable access to the body tissue sandwiched between the inner portion 100 and the outer portion 200 to enable the physician to close the incision in the tissue as further described below. The working window 220 may have any suitable size and/or shape as described above with reference to the working window 120. In one example, the sheet member 210 may be configured as a frame having an inner perimeter extending along a perimeter of the working window 220 and an outer perimeter extending along the outer edge of the sheet member 210.

The external portion 200 may include a coupling member 230, which may be configured to couple the external portion 200 to the internal portion 100 of the medical device as further described below. In one example, the coupling member 230 may include one or more magnetic members, which may be configured to magnetically couple the internal portion 100 and the external portion 200 to one another. For example, the coupling member 230 may include a plurality of magnetic buttons 232 as shown in FIG. 2. The magnetic buttons 232 may be attached to the sheet member 210 and configured generally as described above with reference to the magnetic buttons 132. In one example, the external portion 200 may include a magnetic button 232 corresponding to each magnetic button 132 of the first portion 100. Each magnetic button 132 of the internal portion 100 and the corresponding magnetic button 232 of the external portion may be configured to be magnetically attracted to one another to magnetically couple the internal portion 100 and the external portion 200 to one another. To that end, the magnetic buttons 232 (or other coupling member 230) may be arranged on the sheet member 210 in substantially the same pattern as the magnetic buttons 132 (or other coupling member 130) are arranged on the internal portion 100. This may aid in properly aligning the internal portion 100 and the external portion 200 with one another as further described below.

Although the external portion 200 may be substantially similar to the internal portion 100 in many respects, the external portion 200 may not include a tether. In other words, the external portion 200 may be substantially free of a projection extending outward away from the sheet member 210 as shown in FIG. 2.

Figure 4:
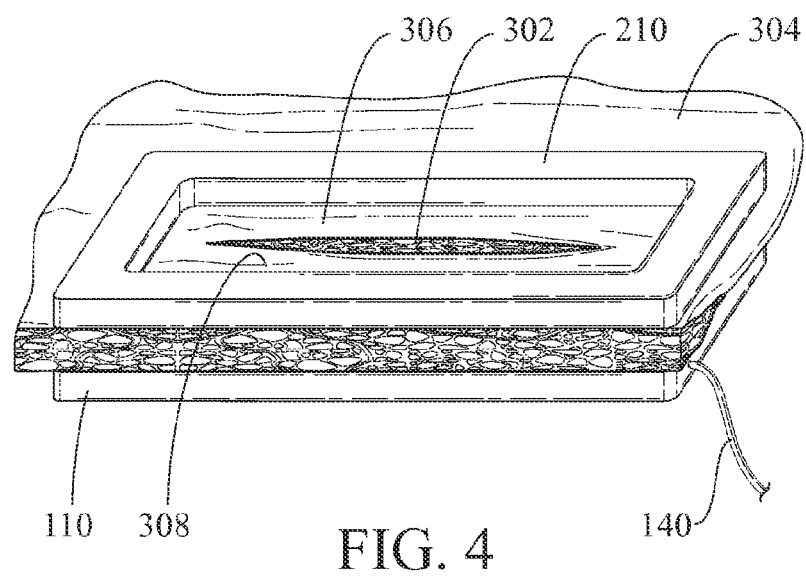

FIGS. 3-4 illustrate the medical device of FIGS. 1-2 in use to approximate tissue planes during a surgical procedure. In one example, the surgical procedure may be a cesarean section. During the cesarean section, an incision 302 may be made through a uterine wall 304 of a patient. A first uterine tissue plane 306 and a second uterine tissue plane 308 may be disposed on opposite sides of the incision 302. After delivery of a child through the incision 302, the internal portion 100 of the medical device may be placed inside the uterus. For example, the internal portion 100 may be introduced into the uterus through the incision 302. The first surface 112 of the sheet member 110 of the internal portion 100 may be placed in contact with an inner surface of the uterine wall 304. The sheet member 110 may be sufficiently flexible that the sheet member 110 may conform to the inner surface of the uterine wall 304. The sheet member 110 may be retained in place on the inner surface of the uterine wall 304 by the weight of the inner cavity and/or manipulation of the sheet member 110 by the physician (e.g., using forceps). The tether 140 of the internal portion 100 of the medical device may be placed through the patient's cervical opening. In other words, the tether 140 may be introduced into the patient's cervical opening such that the tether extends from the sheet member 110 of the internal portion 100 and exits the patient's body through the cervical opening. This may aid in retrieving the internal portion 100 after the incision has been closed as further described below.

With the internal portion 100 of the medical device in place within the uterus, the external portion 200 of the medical device may be placed on an outer surface of the uterine wall 304. The first surface 212 of the external portion may be placed in contact with the outer surface of the uterine wall 304. The external portion 200 may be substantially aligned with the internal portion 100 as shown in FIGS. 3-4. In other words, a portion of the external portion 200 (e.g., the sheet member 210, the working window 220, and/or the coupling member 230) may be aligned with a corresponding portion of the internal portion 100 (e.g., the sheet member 110, the working window 120, and/or the coupling member 130). In one example, each magnetic button 132 (or other coupling member 130) of the internal portion 100 may be aligned with the corresponding magnetic button 232 (or other coupling member 230) of the external portion 200. The attractive force between the magnetic buttons (or other coupling members) may cause the internal portion 100 and the external portion 200 to be coupled (e.g., magnetically coupled) to one another. In one example, the inner perimeter of the sheet member 110 of the internal portion 100 may be substantially aligned with the inner perimeter of the sheet member 210 of the external portion 200 so that the working window 120 is substantially aligned with the working window 220. Additionally, or alternatively, the outer perimeter of the sheet member 110 may be substantially aligned with the outer perimeter of the sheet member 210.

A portion of the uterine wall 304 may be positioned between the coupled first and second portions of the medical device as shown in FIGS. 3-4. In other words, the portion of the uterine wall 304 may be engaged or captured between the first portion 100 and the second portion 200 of the medical device to sandwich the uterine tissue between the first and second portions. This may cause the inner surface of the first uterine tissue plane 306 to be substantially aligned with the inner surface of the second uterine tissue plane 308. Additionally, or alternatively, this may cause the outer surface of the first uterine tissue plane 306 to be substantially aligned with the outer surface of the second uterine tissue plane 308. In other words, sandwiching the uterine wall 304 between the first portion 100 and the second portion 200 of the medical device may aid in approximating the first uterine tissue plane 306 and the second uterine tissue plane 308. The attractive force between the first portion 100 and the second portion 200 of the medical device may retain the first uterine tissue plane 306 and the second uterine tissue plane 308 in alignment with one another while the physician closes the incision 302 as further described below.

With the internal portion 100 and the external portion 200 of the medical device coupled to one another, the working window 120 of the internal portion 100 may be substantially aligned with the working window 220 of the external portion 200. In this manner, the portion of the uterine wall 304 engaged between the first portion 100 and the second portion 200 of the medical device may be accessible through the working window 120 and/or the working window 220. For example, the outer surface of the uterine wall 304 may be accessible through the working window 220 of the external portion 200. Similarly, the inner surface of the uterine wall 304 may be accessible through the working window 120 of the internal portion 100. The internal portion 100 and the external portion 200 of the medical device may substantially surround the incision 302 to aid the physician in manipulating the uterine tissue surrounding the incision 302. In other words, the internal portion 100 may be positioned on the uterine wall 304 such that the incision 302 is positioned within the working window 120. Additionally, or alternatively, the external portion 200 may be positioned on the uterine wall 304 such that the incision 302 is positioned within the working window 220. The internal portion 100 and the external portion 200 may cooperatively support the uterine tissue surrounding the incision 302 and concurrently maintain the first uterine tissue plane 306 in substantial alignment with the second uterine tissue plane 308 while the physician closes the incision as further described below. The uterine tissue may be supported concurrently from inside the uterus and outside the uterus. This may aid in holding the uterine tissue planes together while closing the incision as further described below.

The first uterine tissue plane 306 and the second uterine tissue plane 308 may be pulled together (e.g., with forceps) to pull the incision 302 closed. The physician may close the incision 302 using any suitable technique including, for example, suturing, stapling, bonding, or any other technique. In one example, the physician may close the incision 302 by suturing. The physician may use forceps to hold the uterine tissue while using a needle driver to pass a needle through the tissue to suture the incision closed. The support provided by the internal portion 100 and the external portion 200 of the medical device may aid in holding the uterine tissue in place to reduce the risk of the uterine tissue planes being skewed or misaligned during the suturing process.

Once the incision 302 is closed, the external portion 200 of the medical device may be removed from the uterine wall 304. In other words, the external portion 200 may be lifted away from the outer surface of the uterine wall 304. Additionally, or alternatively, the internal portion 100 of the medical device may be removed from the patient's body. The internal portion 100 and the external portion 200 may be removed in any order or sequence. Upon removal of at least one of the internal portion 100 or the external portion 200 of the medical device from the uterine wall 304, the internal and external portions may be decoupled from one another. In one example, a proximal end of the tether 140 located outside of the patient's body may be grasped, and the tether may be retracted proximally. This may cause the internal portion 100 of the medical device to be pulled proximally through the uterus and toward the cervical opening. Upon reaching the cervical opening, the internal portion 100 may collapse as described above. In other words, the sheet member 110 of the internal portion 100 may be deformed such that the length and/or width of the internal portion 100 may be reduced. In one example, the internal portion 100 may be deformed by contact with the uterine walls and/or the cervical opening. For example, the internal portion 100 may be deformed as it is pulled through the narrowing cervical opening. This may enable the internal portion 100 to pass through the cervical opening and exit the patient's body.

In any of the examples described herein, the sheet member 110 of the internal portion and the sheet member 210 of the external portion 200 may be formed from any suitable material. In one example, the sheet members may be formed from a polymeric material such as, for example, silicone, vinyl, latex, acrylonitrile butadiene styrene (ABS), polyurethane, polyether ether ketone (PEEK), polyethylene terephthalate (PET), polyethylene oxide (PEO), polystyrene, polyamide, polyvinyl chloride (PVC), polytetrafluoroethylene (PTFE), expanded polytetrafluoroethylene (ePTFE), polypropylene, high density polyethylene (HDPE), an elastomer (e.g., a viscoelastic polymer), or any other suitable polymeric material. In another example, the sheet members may be formed from a metallic material such as, for example, a cobalt-chromium alloy (e.g., cobalt-chrome), nitinol, stainless steel, or any other suitable metallic material. In another example, the sheet members may be formed from any other suitable material such as, for example, pyrolytic carbon. Preferably, the sheet members may be formed from a material having a relatively high tear strength. Additionally, or alternatively, the sheet members may be formed from a material having a low modulus, which may aid in removal of the internal portion 100 from the uterus as described above.

The internal portion 100 and the external portion 200 of the medical device may be formed from the same or different materials. In one example, the sheet member 110 of the internal portion 100 may have a durometer that is less than a durometer of the sheet member 210 of the external portion 200. In other words, the sheet member 110 may be formed from a material that is softer (e.g., less stiff or more pliable) than the sheet member 210. The relatively softer sheet member 110 may help to reduce the risk of damaging the uterus and/or the cervical opening during removal of the internal portion 100 from the patient's body. Additionally, or alternatively, the relatively softer sheet member 110 may enable the internal portion 100 to more easily collapse into a reduced length and/or a reduced width configuration for removal from the patient's body. The relatively harder sheet member 210 may add stability to the medical device during approximation of the uterine tissue. Additionally, or alternatively, the relatively harder sheet member 210 may aid in opening and/or adjusting the position of the sheet member 110 within the uterus without directly manipulating the internal portion 100. In other words, the external portion 200 may be manipulated outside of the uterus to manipulate the internal portion 100 positioned inside the uterus (e.g., using the attractive force between the internal portion 100 and the external portion 200) to properly couple the internal portion 100 and the external portion 200 to one another as described above.

The sheet members may be formed using any suitable process. In one example, the sheet members may be formed using a molding process (e.g., injection molding). In another example, the sheet members may be configured as laminate materials. In other words, the sheet members may include a plurality of layers or sheets of material cooperatively forming the sheet members. In another example, the sheet members may be formed as a weave or mesh of filamentary strands or wires (e.g., polymeric or metallic strands or wires). In yet another example, the sheet members may be formed using a combination of two or more of any of the processes described above.

In any of the examples described herein, the magnetic members (e.g., the magnetic buttons, the magnetic strips, or any other magnetic member) may include any type of material capable of producing a magnetic field. Additionally, or alternatively, the magnetic members may include any type of material capable of interacting with a magnetic field. In other words, the magnetic members may include a material that creates a persistent magnetic field (e.g., a magnetically hard material or a permanent magnet) or a material which does not create a persistent magnetic field, but which may be magnetized (e.g., a magnetically soft material). The magnetic members may include any type of magnetic material such as, for example, a magnetic metal or composite (e.g., nickel titanium alloy, stainless steel, iron, nickel, or cobalt), a ceramic material having magnetic properties, a polymeric material coated or impregnated with a magnetic material, or any other type of magnetic material. In one example, the magnetic members may include a rare earth magnet (e.g., a neodymium or a samarium cobalt magnet), which may be plated or coated with a metallic material such as stainless steel. In one example, the magnetic members may include an electromagnet, which may act as a magnet when an electric current is passed therethrough and cease to act as a magnet when the electric current is not passed therethrough. In this manner, the magnetic members may be magnetized and/or demagnetized (e.g., by starting or stopping the electric current) as desired during a medical procedure. The magnetic members may have any suitable magnet strength (e.g., gauss rating or pull strength). The magnet strength may depend on clinical need.

In one example, the magnetic members may be polarized to aid in proper positioning and/or alignment of the internal portion 100 and the external portion 200 of the medical device. For example, the magnetic members 132 positioned along one edge of the internal portion 100 may be polarized in such a way as to be attracted to the magnetic members 232 positioned along the corresponding edge of the external portion 200. In other words, the attraction between the corresponding edges of the internal portion 100 and the external portion 200 may be favored over attraction between non-corresponding edges. Similarly, the magnetic members 132 positioned along an opposite edge of the internal portion 100 may be polarized in such a way as to be attracted to the magnetic members 232 positioned along the corresponding edge of the external portion 200. In this manner, attraction between one or more edges of the internal portion 100 and the corresponding one or more edges of the external portion 200 may be favored to aid in aligning the internal and external portions of the medical device with one another.

The coupling members 130 may be attached to the sheet member 110 of the internal portion 100 of the medical device. Similarly, the coupling members 230 may be attached to the sheet member 210 of the external portion 200 of the medical device. In one example, the coupling members may be attached to a surface (e.g., the first surface or the second surface) of the respective sheet member. The coupling members may be attached to the surface of the sheet members by any suitable method including, for example, adhesive, sutures, staples, clamps, or any other attachment mechanism.

In another example, the coupling members may be encapsulated or embedded within the respective sheet member. For example, the coupling members may be positioned within a void in the sheet member so that the sheet member at least partially surrounds the coupling members. In other words, the coupling members may be overmolded with a polymer material to form the sheet member with the coupling members encapsulated therein. In one example, the coupling members may be disposed on a substrate such as, for example, a surgical mesh. The substrate with the coupling members disposed thereon may be overmolded with a polymer material to form the sheet member with the coupling members (and the substrate) encapsulated therein. The encapsulated coupling members may be entirely surrounded by the sheet member so that no portion of the coupling members is exposed on the exterior surface of the respective interior or exterior portion of the medical device. In this manner, substantially the entire exterior surface of the medical device may be covered by a relatively soft material (e.g., a polymeric material) which may reduce the risk of damaging the body tissue engaged by the medical device as described above.

While use of the medical device has been described herein with reference to approximating uterine tissue during a cesarean section, this disclosure is not so limited. The medical device described herein may be used to approximate planes of any body tissue to aid in closure of an incision therethrough. For example, the medical device may be used to aid in closure of an opening formed in any body cavity having a natural orifice such as, for example, the digestive tract or the urinary tract.

While various embodiments of the invention have been described, the invention is not to be restricted except in light of the attached claims and their equivalents. Moreover, the advantages described herein are not necessarily the only advantages of the invention and it is not necessarily expected that every embodiment of the invention will achieve all of the advantages described.

We claim:

1. An apparatus for approximating planes of a body tissue during a medical procedure, the apparatus comprising:
   an internal portion implantable within a body of a patient and comprising a first flexible sheet member comprising a first engaging surface to engage an internal surface of the body tissue, a first magnetic member, and a first working window through the first flexible sheet member; and
   an external portion comprising a second flexible sheet member comprising a second engaging surface to engage an external surface of the body tissue opposite the internal surface of the body tissue, a second magnetic member, and a second working window through the second flexible sheet member;
   wherein the first magnetic member and the second magnetic member are attracted to one another to magnetically couple the internal portion and the external portion to one another and capture the body tissue between the internal portion and the external portion; and
   wherein, with the internal portion and the external portion magnetically coupled to one another, the first working window is substantially aligned with the second working window to enable access to the internal surface of the body tissue through the first working window and access to the external surface of the body tissue through the second working window.

2. The apparatus of claim 1, wherein the internal portion further comprises a tether extending from the first flexible sheet member for removing the internal portion from the body.

3. The apparatus of claim 1, wherein the first flexible sheet member is movable between an open configuration in which the first flexible sheet member is substantially planar and a collapsed configuration in which at least a portion of an outer edge of the first flexible sheet member is gathered inward toward a central portion of the first flexible sheet member.

4. The apparatus of claim 1, wherein the first magnetic member comprises a first plurality of magnets positioned between the first working window and an outer edge of the first flexible sheet member and spaced from one another about a perimeter of the first flexible sheet member.

5. The apparatus of claim 4, wherein the second magnetic member comprises a second plurality of magnets positioned between the second working window and an outer edge of the second flexible sheet member and spaced from one another about a perimeter of the second flexible sheet member.

6. The apparatus of claim 5, wherein, with the internal portion and the external portion magnetically coupled to one another, each of the first plurality of magnets is substantially aligned with a corresponding one of the second plurality of magnets.

7. The apparatus of claim 5, wherein at least one of the first plurality of magnets is polarized, at least one of the second plurality of magnets is polarized, and the polarized magnets are magnetically attracted to one another to aid in aligning the internal portion and the external portion with one another.

8. The apparatus of claim 1, wherein the first magnetic member is encapsulated within the first flexible sheet member.

9. The apparatus of claim 1, wherein the first flexible sheet member comprises a first polymeric material having a first durometer, the second flexible sheet member comprises a second polymeric material having a second durometer, and the second durometer is greater than the first durometer.

10. The apparatus of claim 1, wherein the first flexible sheet member comprises a frame extending along a perimeter of the first working window, and the second flexible sheet member comprises a frame extending along a perimeter of the second working window.

11. An apparatus for approximating planes of a body tissue during a medical procedure, the apparatus comprising:
an internal portion comprising a first flexible sheet member comprising a first engaging surface to engage an internal surface of the body tissue and a first working window disposed in the first flexible sheet member; and
an external portion comprising a second flexible sheet member comprising a second engaging surface to engage an external surface of the body tissue opposite the internal surface and a second working window disposed in the second flexible sheet member;
wherein, in use, the internal portion and the external portion are magnetically coupled to one another to sandwich a portion of the body tissue between the first engaging surface of the internal portion and the second engaging surface of the external portion, and at least a portion of the first working window is substantially aligned with a corresponding portion of the second working window.

12. The apparatus of claim 11, wherein the internal portion further comprises an elongate tether extending from the first flexible sheet member.

13. The apparatus of claim 12, wherein the elongate tether comprises a length of tubing.

14. The apparatus of claim 11, wherein the internal portion comprises a plurality of magnetic buttons attached to the first flexible sheet member and spaced about the first working window, the external portion comprises a plurality of magnetic buttons attached to the second flexible sheet member and spaced about the second working window.

15. The apparatus of claim 14, wherein each magnetic button of the internal portion is encapsulated within the first flexible sheet member such that no portion of the magnetic button extends outside of the first flexible sheet member.

16. The apparatus of claim 11, wherein at least one of the internal portion or the external portion comprises a magnetic member attached to the respective first flexible sheet member or second flexible sheet member, and the magnetic member is magnetically attracted to the other of the internal portion or the external portion to magnetically couple the internal portion and the external portion to one another.

17. The apparatus of claim 11, wherein at least one of the internal portion or the external portion comprises a magnetic member comprising a magnetically hard material, and the other of the internal portion or the external portion comprises a magnetic member comprising a magnetically soft material.

18. The apparatus of claim 11, wherein the first flexible sheet member comprises a hardness that is less than a hardness of the second flexible sheet member.

19. The apparatus of claim 11, wherein the internal portion comprises a first magnetic member and a second magnetic member, the external portion comprises a third magnetic member and a fourth magnetic member, the first magnetic member is magnetically attracted to the third magnetic member and magnetically repelled by the fourth magnetic member, and the second magnetic member is magnetically attracted to the fourth magnetic member and magnetically repelled by the third magnetic member.

* * * * *